United States Patent [19]

Chazallet

[11] Patent Number: 5,453,883
[45] Date of Patent: Sep. 26, 1995

[54] APPARATUS FOR PRODUCING A MONOCHROMATIC LIGHT BEAM

[76] Inventor: Frédéric Chazallet, 24, Bld National, 13003 Marseille, France

[21] Appl. No.: 157,930

[22] Filed: Nov. 26, 1993

[30] Foreign Application Priority Data

Dec. 4, 1992 [FR] France ................................ 92 14895

[51] Int. Cl.6 ................................ G02B 5/22; G01J 1/00
[52] U.S. Cl. ........................ 359/890; 359/889; 359/589; 362/293
[58] Field of Search ................................ 359/887, 889, 359/890, 891, 589; 362/293; 250/365

[56] References Cited

U.S. PATENT DOCUMENTS

| | | |
|---|---|---|
| 3,457,002 | 7/1969 | Magrath . |
| 4,342,516 | 8/1982 | Chamran et al. ................ 356/332 |
| 4,385,344 | 5/1983 | Gonser ................................ 362/32 |
| 4,396,288 | 8/1983 | Helphrey ........................ 356/326 |
| 4,860,172 | 8/1989 | Schlager et al. ................ 362/32 |

FOREIGN PATENT DOCUMENTS 0488333  6/1992  European Pat. Off. .

*Primary Examiner*—Loha Ben
*Assistant Examiner*—Audrey Y. Chang
*Attorney, Agent, or Firm*—Dvorak and Traub

[57] ABSTRACT

An apparatus for producing a substantially monochromatic light beam for chromotherapy and/or actinotherapy is disclosed ; the apparatus comprises a transportable housing including a light source, which housing includes a movable heterogeneous interference filter mounted on a support that is displaceable by means of a motor, said apparatus further including a wand enabling said light beam to be directed onto a zone to be treated, and said apparatus also including transmission means for conveying said light beam from said housing to said wand, said housing including an infrared filter interposed between said light source and said interference filter.

18 Claims, 6 Drawing Sheets

APPARATUS FOR PRODUCING A MONOCHROMATIC LIGHT BEAM

The present invention relates to apparatus for producing a monochromatic light beam and is intended for chromotherapy, actinotherapy, chromatotherapy, or chromopuncture.

The field of the invention is that of apparatuses for therapeutic treatment of the human or animal body by means of light rays, and in particular rays in the visible region of the spectrum.

BACKGROUND OF THE INVENTION

It is known that all or a part of the human or animal body can be exposed to visible light radiation in particular for therapeutic purposes, in particular for treating skin diseases or for treating states of fatigue, and also for treating various infections and traumatisms.

Patent application FR 2 668 068 (Lerner), for example, discloses a method of exposing a body to monochromatic light rays and apparatus for implementing the method; in the method described in that document, the body to be treated is illuminated in successive monochromatic lighting sequences delivered by individual monochromatic light sources which are switched on sequentially in order to cover the light spectrum.

The apparatus described in that document for implementing the method includes an upper lighting panel and a lower bed constituted by a transparent sun bed situated above monochromatic radiation tubes identical to those in the upper panel.

Patent application EP-A-488333 filed on 28/11/91 describes an apparatus for the chromatic exitation of quartz elements for therapeutic purposes, which comprises a light generator providing luminous radiation of variable intensity and chromatism, which light generator is controlled by means of a computer and is equipped with filters; an applicator including crystals of quartz is connected to the computer by means of optical fibers.

OBJECTS AND BRIEF SUMMARY OF THE INVENTION

An object of the present invention is to provide apparatus for producing a monochromatic light beam intended in particular for actinotherapy and that enables selective treatment to be performed, i.e. that enables a determined zone of relatively small dimensions of the human or animal body to be treated selectively (on its own), and that also makes it possible to treat said zone of the human body by means of radiation that is substantially monochromatic, i.e. radiation in which the major portion of the energy is concentrated in a narrow band of frequencies or wavelengths.

The invention also consists in providing such apparatus that is easy for a practitioner to manipulate and that is suitable for being manufactured at moderate expense.

The solution to the problem posed consists in providing apparatus for producing a substantially monochromatic light beam that is situated essentially in the visible light spectrum and/or in the near infrared and/or in the near ultraviolet, which apparatus is particularly intended for chromotherapy and/or for actinotherapy; the apparatus comprises a transportable housing including (containing) a light source (providing non-coherent light over a broad spectrum, such as an incandescent lamp using at least one halogen gas, and at a power of about 50 watts, for example), which housing includes (contains) bandpass optical filter means of narrow bandwidth, and having a center wavelength (or corresponding frequency) that is preferably continuously variable, and includes (contains) means for modifying (preferably continuously) said center wavelength, which apparatus further includes a wand (or pointer) enabling said light beam to be directed onto a zone of the skin of the human body to be treated and suitable for being positioned at a predetermined distance from said skin zone to be treated; said apparatus also including means for conveying said light beam produced by said light source between said housing and said wand.

Advantageously, the said bandpass optical filter means of variable center wavelength comprises an interference filter that is movable and heterogeneous (i.e. in which the center wavelength is not constant over the working area of said filter).

Advantageously, said interference filter is in the form of a strip that is quite narrow (in which the ratio of length L1 to width L2 is not less than 5, for example), that is substantially rectilinear, and that is capable of being curved about a radius R7 (e.g. of the order of 50 mm); said strip includes successive alternating thin film deposits of at least two predetermined materials (e.g. such as cryolite and zinc sulfide ZnS), which deposits may be made on a flexible and transparent support or plate from which said strip is subsequently cut out and which is made of a plastics material such as polycarbonate, polymethyl methacrylate (PMMA) or triacetate, said strip being mounted on a cylindrical support about an axis XX1 that is suitable for being rotated about said axis by a motor, preferably a stepper motor integrated in said housing.

Advantageously, said housing includes (contains) an infrared filter (i.e. an infrared blocking or absorbing filter which is a lowpass filter in terms of wavelength, or in other words a filter that absorbs wavelengths that are greater than or equal to 1 micrometer) that is interposed between said light source and said interference filter.

In other words, the solution to the problem formulated consists in providing an apparatus intended for actinotherapy, the apparatus generating a substancially monochromatic light beam, the apparatus comprising a portable casing (housing) including a light source, which casing includes a movable heterogeneous interference filter which is fastened to a support, which support is movable by means of a motor; the apparatus further comprises a handle and transmission means for conveying said light beam from said casing to said handle, said apparatus further comprising an infrared filter which is inserted between said light source and said interference filter.

The apparatus may further comprise a red bandpass filter which is serial mounted on said interference filter with respect to said light beam, said red bandpass filter transmitting light radiations which wavelengths are greater than about 650 nanometers and absorbing light radiations which wavelengths are smaller than about 600 nanometers.

The apparatus may further comprise a blue bandpass filter which is serial mounted on said interference filter with respect to said light beam, said blue bandpass filter transmitting light radiations which wavelengths are comprised between about 425 nanometers and about 500 nanometers and absorbing light radiations which wavelengths are comprised between about 550 nanometers and about 750 nanometers.

Said red bandpass filter and said blue bandpass filter can be gelatin filters, which are mounted or stuck on said interference filter or on said support; said red and blue bandpass filters can respectively extend over a first area and a second area of said support, which said first and second areas (or which said red and blue filters) are respectively facing a first part and a second part of said interference filter, said first part of said interference filter transmitting light radiations which wavelengths are greater than about 650 nanometers, said second part of said interference filter transmitting light radiations which wavelengths are smaller than about 500 nanometers Advantageously, said infrared filter is constituted (or comprises) a thick glass plate, which thickness is about 1 to 5 millimeters, which glass plate is mounted perpendicular to axis of symetry of light beam produced by said light source, intrinsic transmission rate of said glass plate being smaller or equal to 2% (two percent) for radiations which wavelength are greater than 1000 nanometers and smaller than 3000 nanometers.

Advantageously, said apparatus includes (integrated in said housing) a microprocessor central unit, a detector for detecting the position of said filter and/or of said filter support, recording means (such as a memory, at least) for recording at least two calibration data pairs, which calibration data pairs include at least a first pair comprising first position data of said filter and at least a first corresponding center wavelength (which may be measured by calibration apparatus), and include at least one second calibration data pair comprising second position data for said filter and a corresponding second center wavelength (which may be measured by said calibration apparatus), said calibration data pairs being suitable for being recorded in said memory and being protected against deletion.

Advantageously, said apparatus includes means for recording a plurality of positions for said filter corresponding to center wavelengths that the user desires to store.

Advantageously, said apparatus includes means for recording a plurality of data pairs, each data pair comprising a first data item relating to a duration for illumination and a second data item corresponding to a predetermined corresponding center wavelength.

Advantageously, said apparatus includes means for interpolating (e.g. by linear interpolation) between said calibration data pairs so that when said apparatus is to produce said monochromatic light beam around a desired given center wavelength, a value representative of said determined or desired center wavelength is input, and said interpolation means determine a position, e.g. an angular position, for said filter and/or for said filter support, enabling said desired center wavelength to be obtained by interpolation between previously recorded calibration data pairs.

Advantageously, the −3 dB bandwidth of said passband of said filter means is of the order of 10 nanometers, over a band of wavelengths that extends, for example, from 400 (or 450) nanometers to 650 (or 700) nanometers, and said apparatus makes it possible to obtain resolution (or accuracy or error relating a desired center wavelength to a center wavelength as obtained) that is of the order of 10 nanometers.

Advantageously, said housing is generally in the form of a pyramid, and said apparatus includes a digital interface for communication with an external computer, and includes a keypad enabling data to be input, in particular data relating to the desired center wavelength and duration of exposure, and it includes a display serving, in particular to display the wavelength of said monochromatic light beam corresponding to the current position of said moving interference filter.

The apparatus of the invention for producing a monochromatic light beam has numerous advantages: the apparatus of the invention enables a determined zone of the human or animal body to be selectively treated at one or mope center wavelengths; and mope precisely it enables it to be treated with predetermined lighting sequences using a light beam in which the major fraction of the energy is concentrated in spectrum or wavelength bands that ape narrow, e.g. having a bandwidth of the order of 10 nanometers.

The invention makes it possible to obtain such devices that can be manufactured at low cost, which may be portable or transportable; selective treatment of a predetermined zone of the human body to be treated is made easier, in particular because of said wand (handle) that includes an optical system for focusing the output light beam, which wand is connected to said housing containing said light source via a connection device such as an optical fiber cable that makes it easy for the practitioner to manipulate said wand. The apparatus of the invention for producing a monochromatic light beam is also easy to use by virtue of its interface means with the user which makes it simple to select desired wavelengths and/or lighting sequences. Ease of use can be further increased by connecting apparatus of the invention to a computer or a controller that is used to keep a permanent record of data relating to treatment specifically for a given patient and/or for a given disease. When disease data is on record, once the pathology to be treated has been selected, the apparatus can operate automatically under the control of said computer, to perform a lighting sequence of predetermined durations and center wavelengths (i.e. previously recorded in the memory of the computer) that correspond to said pathology.

An apparatus of the invention comprises a light structure which comprises said interference filter mounted on said support, which structure can be precisely and quickly displaced by an electric motor with a low power consumption.

Because of specific features of said infrared filter and when using a fan for cooling parts situated in said casing, a compact apparatus is obtained, in which temperature increase (or heat) produced by infrared radiations of said light source is removed from said casing by an air flow which is blowed by said fan.

Because of said movable heterogeneous interference filter, center wavelength of output light beam can be continuously varied.

BRIEF DESCRIPTION OF THE DRAWINGS

The numerous advantages provided by the invention will be better understood from the following description that refers to the accompanying drawings which show a particular embodiment of apparatus of the invention, but without limiting the invention thereto.

MORE DETAILED DESCRIPTION

Figure 5:
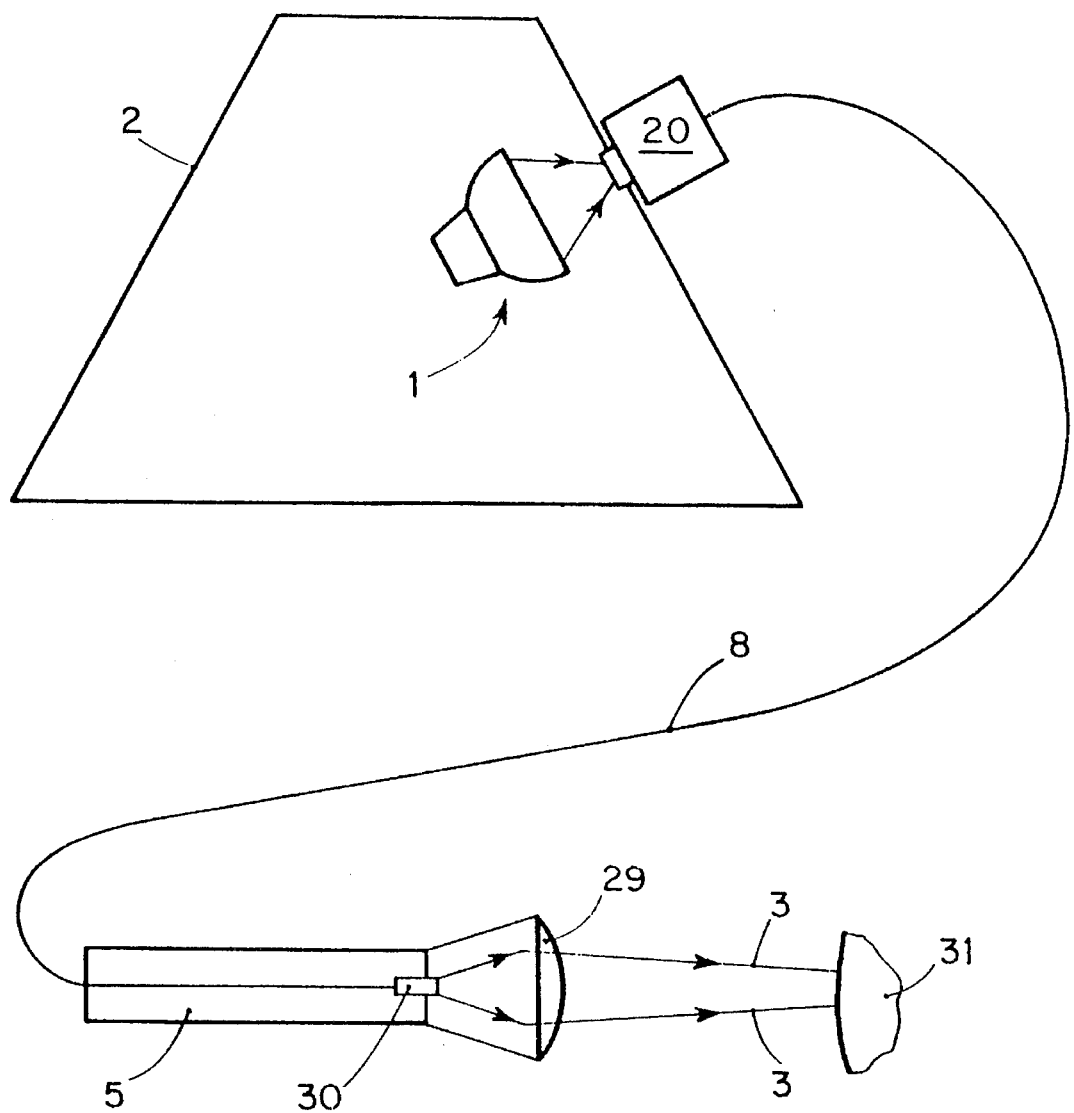
FIG. 5 is a diagram showing the main components of apparatus of the invention and the way in which they are implemented.

With reference to FIG. 5, it can be seen that apparatus of the invention essentially comprises firstly a housing 2 that is preferably in the form of a truncated pyramid, which housing 2 includes a light source 1 that emits a light beam that is suitable for directing onto a target zone 31 of the body of a patient to be treated by means of an optical fiber cable 8 connected to said housing 2 by means of a connector 20, which cable makes it possible to transmit said light beam emitted by said light source 1 to a wand 5 provided with an outlet connector 30 connected to said optical fiber cable 8, which outlet connector 30 enables a beam 3 to be produced at the outlet from said optical fiber cable and which preferably passes through a lens 29 for focusing said beam 3 onto said predetermined zone of the body of the patient to be treated.

Because of the general configuration of the apparatus of the invention, said wand makes it possible to focus said monochromatic light beam obtained at the outlet from the device at a distance as measured between said outlet optical system 29 of said wand and said zone to be treated that may be less than 1 meter so as to produce a light spot or mark on said zone to be treated having a diameter of a few centimeters or a few tens of centimeters; handling of said wand is limited solely by the length of the optical fiber cable 8 which is Flexible and lightweight, thus enabling the zone of the body that is to be treated to be treated selectively by displacing said wand relative to said housing while leaving said housing in a fixed position.

Figure 2:
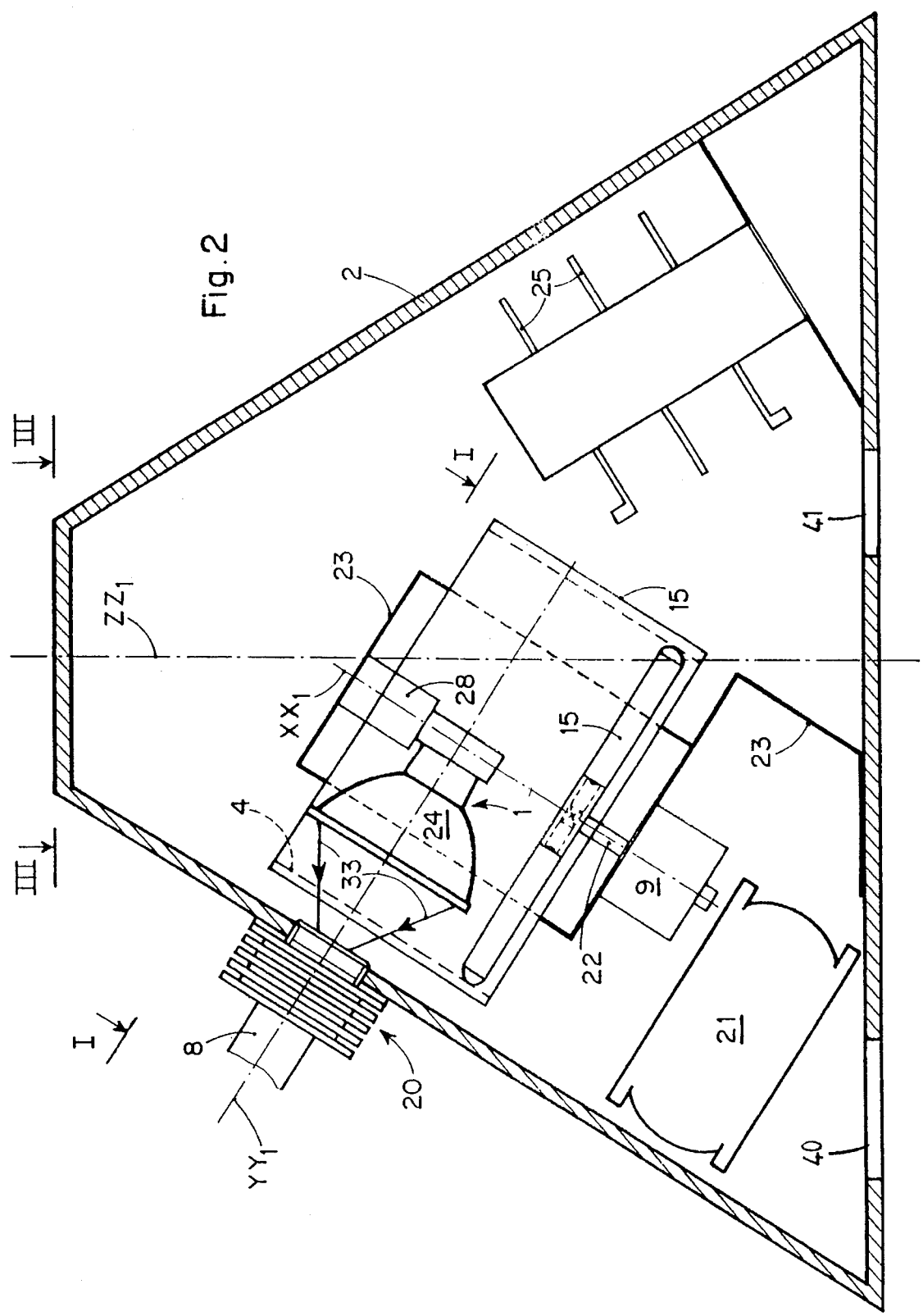
FIG. 2 is a longitudinal vertical section through one embodiment of a housing for apparatus of the invention.

With reference to FIG. 2, it can be seen that said housing 2 includes said light source 1 that may be constituted, for example, by a halogen lamp provided with a dichroic reflector 24 and mounted in stationary manner inside said housing by means of a support 28 which is in turn fixed to a support 23 that is itself fixed to said housing 2.

Said support 23 may also support a motor 9 for rotating a support 15 for a filter 4 about an axis XX1, which filter is preferably an interference filter. Said support 15 is preferably in the form of a cylindrical drum that is open at its top end so that the said light source 1 can be received in the space situated inside said cylindrical drum and can emit an initial light beam 33 along an optical axis YY1 that is substantially perpendicular to said axis of rotation XX1 of said filter-supporting drum. Said initial beam 33 may propagate through said interference filter 4 so as to terminate at said optical connector 20 which is situated at a first end of said optical fiber cable 8 that connects said housing 2 to said operating wand (not shown in this figure).

This figure also shows that said housing contains electronic cards 25 that receive means for controlling and monitoring the apparatus, and that it may also include a cooling fan 21 for said lamp and/or said filters and/or said electronic cards; said fan produces an air flow, where air enters said casing (housing) 2 by an opening 40 and comes out of said casing by an opening 41; said openings 40,41 are provided in a wall of said casing.

Figure 1:
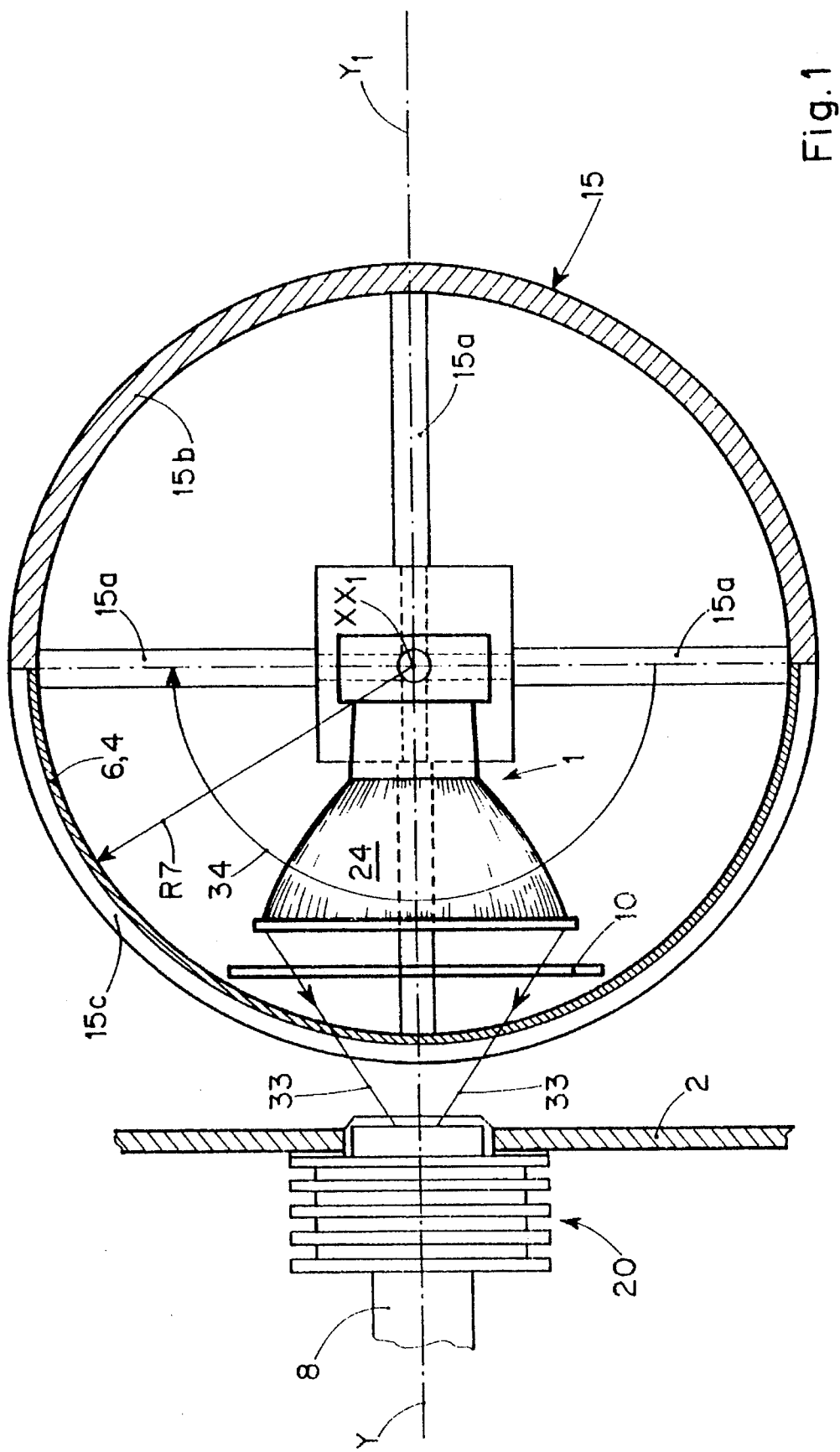
FIG. 1 is a plan view showing the main component parts of the device for emitting a monochromatic beam of variable wavelength in apparatus of the invention, with FIG. 1 being a view on I—I of FIG. 2.

With reference to FIG. 1, it can be seen that in a preferred embodiment, said interference filter 4 is in the form of a strip 6 curved about a radius R7 that may be of the order of about 10 centimeters, for example, which strip extends around half a circumference in a portion 15C of said drum-shaped moving support 15. Said portion 15C constitutes a window provided in the periphery of said drum such that said light beam 33 from said light source 1 can pass through said interference filter regardless of the angular position taken up by said support 15 of the filter when said support 15 as driven by said motor (not shown) rotates about said axis of rotation XX1 between two extreme positions separated by an angle 34 of maximum deviation or rotation for said support 15 (which angle preferably lies in the range 90° to 270°).

Advantageously, an infrared filter 10 is interposed between said light source 1 provided with said reflector 24 (which is mounted in stationary manner relative to said housing 2 that is shown in part) and said moving filter 4 mounted on said moving support 15, so as to intercept a fraction of the light flux situated in the infrared range and thus avoid overheating said interference filter 4.

This figure also shows that said optical connector 20 mounted on the wall 2 of said housing and situated at one end of said optical fiber cable 8 is designed to convey said beam 33 after it has passed through said interference filter 4.

This figure also shows that the general optical axis YY1 of the apparatus is situated in a plane perpendicular to said axis of rotation XX1 of said filter 4 and/or of said filter support 15, which filter support 15 is generally in the form of a thin-walled tube and is provided with diametrically-extending stiffeners 15A enabling it to be secured to the shaft of said motor (not shown).

Figure 3:
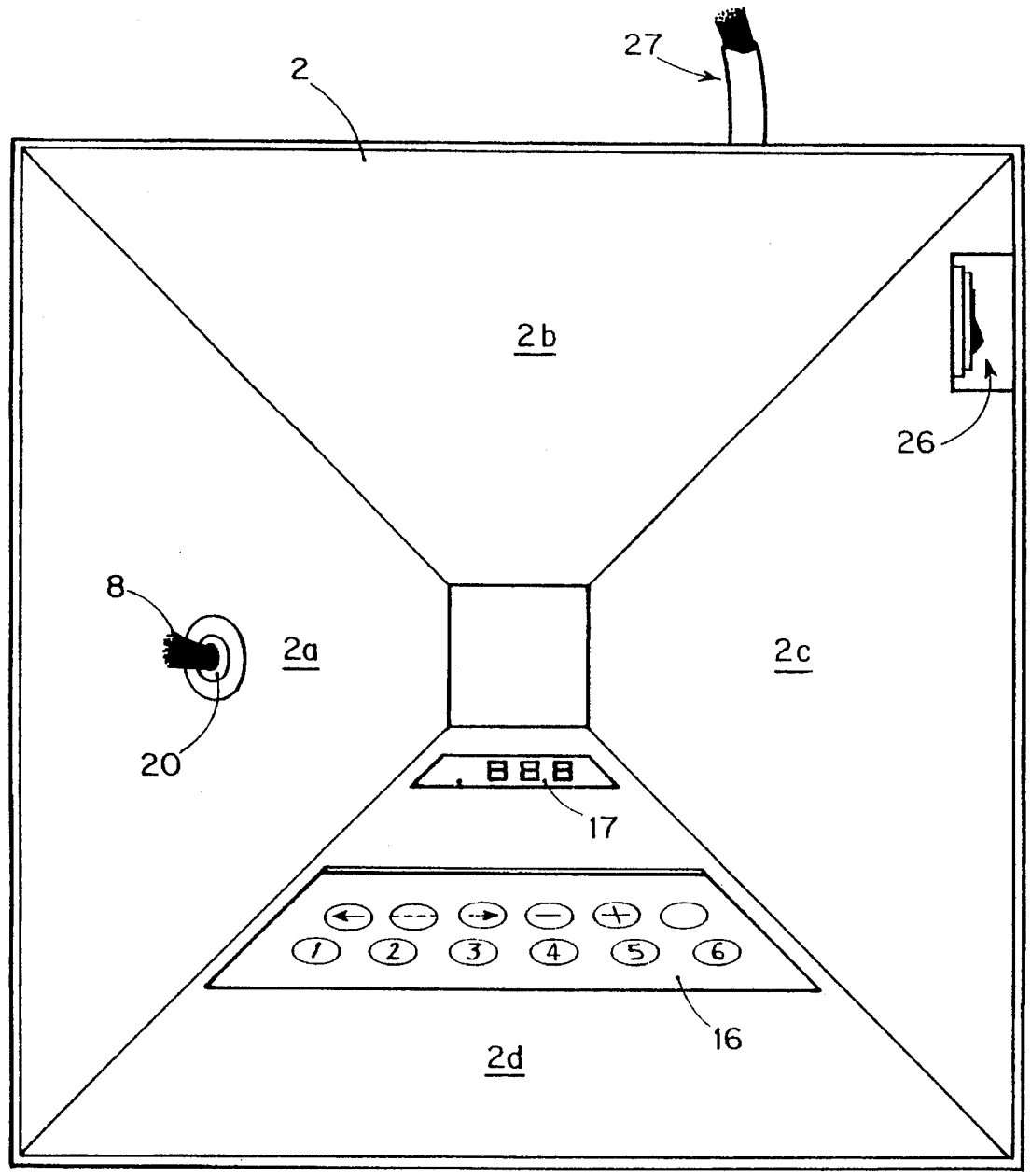
FIG. 3 is a view on III—III of FIG. 2 and constitutes a plan view of a housing for apparatus of the invention.

With reference to FIG. 3, it can be seen that said housing 2 is in the form of a truncated pyramid having four lateral faces 2a, 2b, 2c, and 2d. The face 2a receives said connector 2 that is situated at the end of said optical fiber cable 8; said face 2c receives an ON/OFF control switch 26 for said apparatus that may be powered by means of an electrical power supply cable 27.

Said face 2d may receive a display 17 suitable, for example, for displaying the current center wavelength, i.e. the wavelength corresponding to the current or present position of said filter support (reference 15 in FIGS. 1 and 2). Said face 2d also includes a keypad 16 enabling the user or practitioner to select the wavelength that may have previously been recorded and/or to control the various operating parameters of the apparatus.

Figure 4:
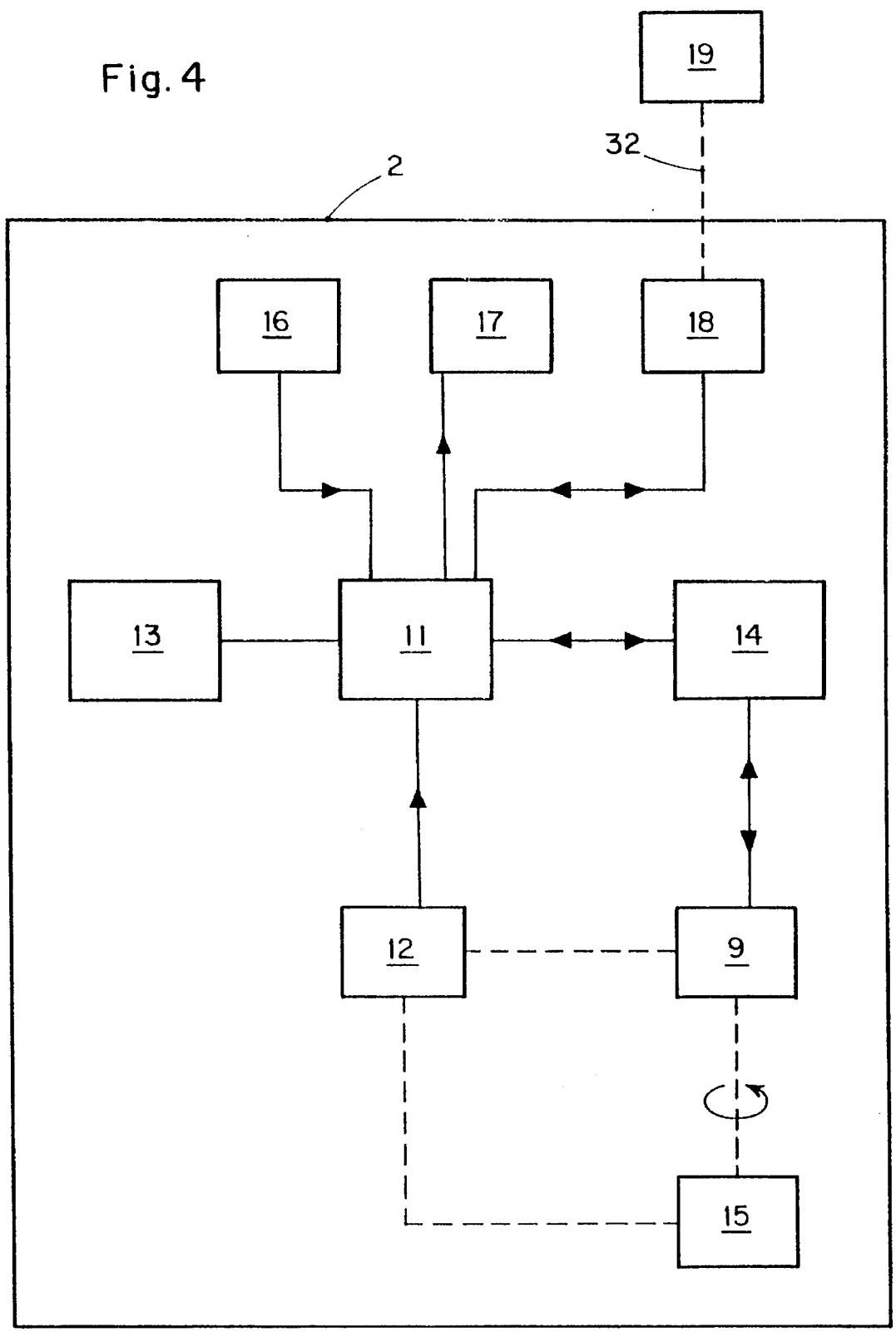
FIG. 4 is a block diagram of the main components of the monitoring and control means for apparatus of the invention.

With reference to FIG. 4, it can be seen that said control and monitoring means of the apparatus (which may be implemented on said electronic cards referenced 25 in FIG. 2) may be essentially constituted by a control unit 11, e.g. comprising a microprocessor, connected to a memory 13 in which the following may be stored: said calibration values of the apparatus and said predetermined and stored values of the angular position of said filter support and of the corresponding center wavelengths. The microprocessor control unit 11 may be connected to an interface and power control module 14 for said motor 9 which may be a stepper motor suitable for rotating said support 15 of the interference filter. A detector 12 for detecting the position of the shaft of said motor and/or of said filter support is connected to said control unit 11 and enables it to be aware at all times of the position of said support so as to be able to deduce therefrom the current center wavelength corresponding to said current position of said filter support relative to said calibration values.

The position monitoring means may comprise said detector 12 detecting an origin (or "zero") position, e.g. by means of a mechanical or an optical sensor, together with means for counting the number of steps performed by said motor.

Said control unit 11 is also connected to said keypad 16 and to said display 17, and it may advantageously be connected via a digital interface 18 to an external computer 19 via connection means 32. The components shown in FIG. 4 (apart From said computer) are integrated within the housing 2 of the apparatus of the invention.

Figure 6:
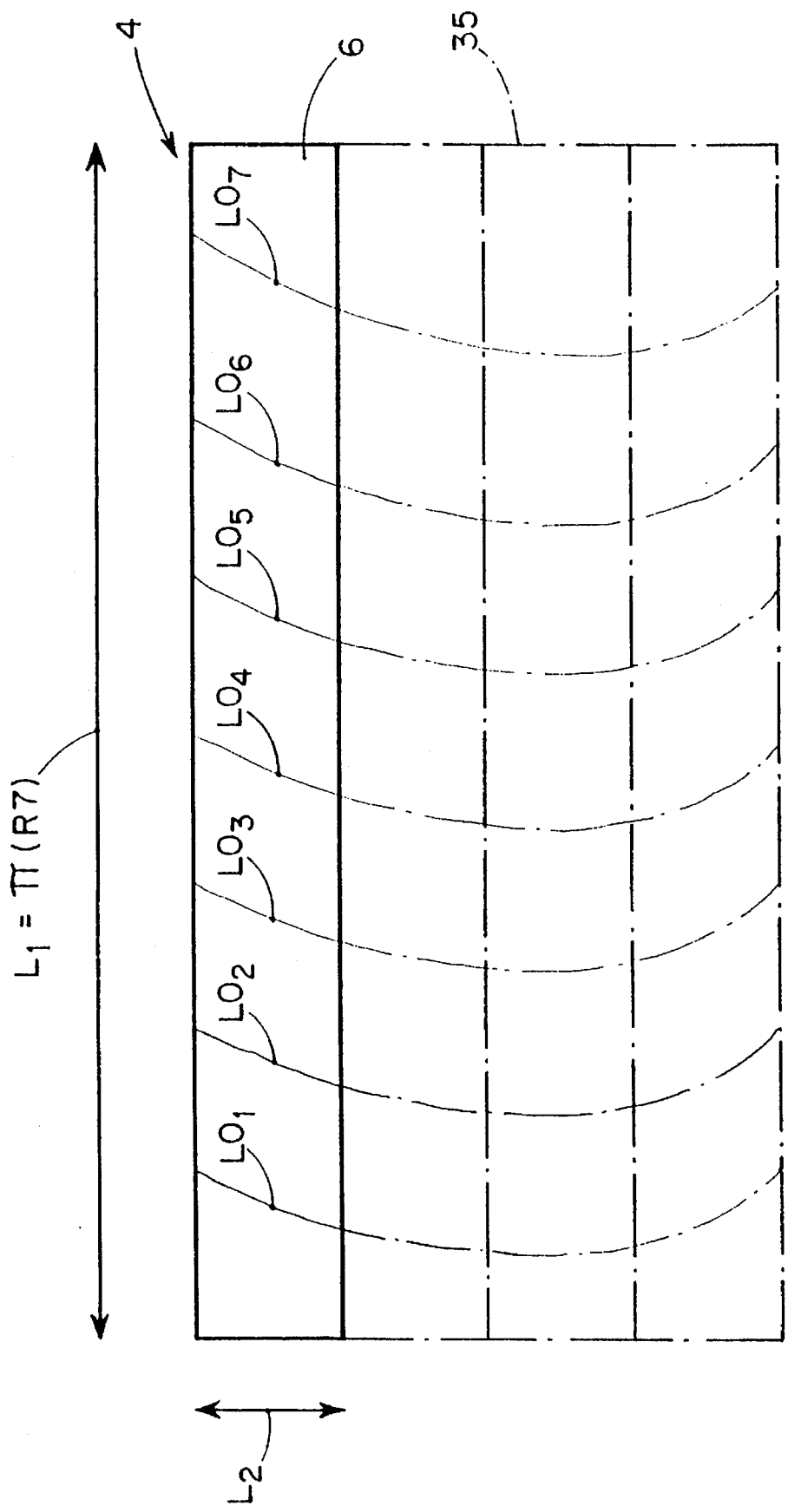
FIG. 6 shows a preferred implementation of an interference filter in the form of a strip and suitable for use in apparatus of the invention.

With reference to FIG. 6, it can be seen that in a preferred embodiment of said interference filter 4, the filter is in the form of a rectilinear elongate strip 6 of width L2 that is small relative to its length L1 which is itself substantially equal to the fraction of the circumference (e.g. half the circumference) that corresponds to said radius marked R7 in FIG. 1, and that is capable of being curved around said filter support.

Said interference filter 4 that is in the form of a strip 6 may be obtained by being cut out from a plate 35 on which thin films of at least two materials suitable For making said interference filter have been deposited, with said deposition giving rise to spatial variations (in the plane of said plate 35) in said thin film deposits because of the relative positions of said plate and the sources from which said materials are sublimed, and said variations in the deposits give rise to spatial variations (or gradients) in the center wavelengths. As shown in FIG. 6, in a zone of said strip 6 (forming a support for said interference filter 4) that is situated to the left of FIG. 6, said zone may correspond to a center wavelength of the passband of said filter that corresponds to a first wavelength value $L0_1$. When the said strip 6 is moved From left to right with reference to FIG. 6, it is thus possible to determine zones or segments that correspond to other passband center wavelengths for said interference filter, which wavelengths are respectively referenced $L0_2$, $L0_3$, $L0_4$, $L0_5$, $L0_6$, and $L0_7$, and said values increase or decrease in a manner that is substantially continuous. Thus, when said light beam from said light source passes through said strip 6 forming the support of the interference filter 4 in a zone close to the zone referenced $L0_1$, the output beam after passing through said filter is substantially centered on a wavelength equal to said wavelength $L0_1$, which wavelength can be measured in the factory while calibrating the apparatus so as to mitigate difficulties associated with repeatability and with variations that may be caused by the geometry of the thin film deposits over different strips 6 cut out from said plate 35.

It is thus possible to obtain substantially continuous variation in the center wavelength of said light beam that has passed through said interference filter merely by substantially continuous rotation (or displacement) of said filter and/or of said filter support.

I claim:

1. An apparatus for producing a substantially monochromatic light beam for chromotherapy and/or actinotherapy, the apparatus comprising:

a transportable housing;

a non-coherent light source which emits light over a broad spectrum;

heterogeneous interference filter with a center wavelength that varies over a working area of the heterogeneous interference filter, the heterogeneous interference filter mounted on a movable support;

a motor for moving the movable support under control of a microprocessor; and a wand enabling said light beam to be directed onto a zone to be treated, and said apparatus also including transmission means for conveying said light beam from said housing to said wand, said housing including an infrared filter interposed between said light source and said interference filter.

2. An apparatus according to claim 1 further comprising a red bandpass filter and a blue bandpass filter which are serial mounted on said interference filter.

3. An apparatus according to claim 1 wherein said infrared filter comprises a thick glass plate.

4. An apparatus according to claim 1, including a digital interface for communicating with an external computer, a keypad enabling data to be input concerning the desired duration and center wavelength of an exposure, and a display for displaying the wavelength of said light beam.

5. An apparatus according to claim 1, wherein said interference filter is in the form of a narrow strip that is substantially rectilinear, that is suitable for being curved around a radius, and that is mounted on a cylindrical support about an axis XXI that is suitable for being rotated about said axis by a stepper motor integrated in said housing.

6. An apparatus according to claim 1, including a microprocessor central unit, a position detector for detecting the position of said filter and/or of said filter support, means for recording at least two calibration data pairs, a first calibration data pair comprising a first interference filter position data and a first corresponding center wavelength data, a second calibration data pair comprising a second interference filter position data and a second corresponding center wavelength data.

7. An apparatus according to claim 1, including means for recording a plurality of interference filter position data items and a plurality of corresponding output light beam center wavelengths.

8. An apparatus according to claim 1, including means for recording a plurality of data pairs, each of the data pairs comprising a first data relating to a duration of exposure and a second data relating to a corresponding predetermined output light beam center wavelength.

9. An apparatus according to claim 6, including interpolation means for performing linear interpolation between said calibration data pairs so that when it is desired for said apparatus to produce said monochromatic light beam centered on a determined center wavelength, a value representing said determined center wavelength is input and said interpolation means determine a position for said interference filter and/or for said support that enables said desired center wavelength to be obtained, this being done by performing interpolation between previously recorded calibration data pairs.

10. An apparatus according to claim 1, wherein bandwidth of said interference filter is of the order of 10 nanometers, within a band of wavelengths lying in the range 400 nanometers to 650 nanometers, and said apparatus enables resolution to be obtained that is of the order of 10 nanometers.

11. An apparatus according to claim 1, wherein said housing is in the form of a pyramid.

12. An apparatus according to claim 1 wherein a cooling fan is included in said housing.

13. An apparatus for producing a substantially monochromatic light beam for chromotherapy and/or actinotherapy, the apparatus comprising:

a light source for emitting a light beam along a path;

a heterogeneous interference filter formed of a strip having adjacent zones, wherein a center wavelength of the heterogeneous interference filter varies substantially continuously over the adjacent zones;

a movable filter support for selectively positioning a zone of the heterogeneous interference filter in the path of the light beam, wherein the light beam is transmitted through the zone of the heterogeneous interference filter to obtain a light beam having a center wavelength corresponding to the center wavelength of the zone, and the center wavelength of the light beam is continuously variable by selectively positioning a different zone of the heterogeneous filter in the path of the light beam; and a wand coupled to the light beam transmitted through the heterogeneous interference filter by an optical transmission cable, wherein the wand directs the light beam onto a target zone.

14. An apparatus according to claim 13 wherein the heterogeneous interference filter is a rectilinear elongate strip formed in a curve-shape with a constant radius, and wherein the movable filter support is rotatable about an axis to position different zones of the heterogeneous filter in the path of the light beam.

15. An apparatus according to claim 13 further comprising an infrared filter interposed between the light source and the heterogeneous interference filter in the path of the light beam.

16. An apparatus according to claim 13 wherein the center wavelength of the heterogeneous interference filter increases from a first end of the strip toward a second end of the strip.

17. An apparatus according to claim 13 further comprising a bandpass filter disposed on the heterogeneous interference filter in the path of the light beam.

18. An apparatus according to claim 14 further comprising a bandpass filter disposed on the heterogeneous interference filter in the path of the light beam.

* * * * *